US011369546B2

(12) United States Patent
Gall et al.

(10) Patent No.: US 11,369,546 B2
(45) Date of Patent: Jun. 28, 2022

(54) CAPSULE SOCKET FOR TWO-PIECE CAPSULES AND SOCKET SYSTEM

(71) Applicant: Harro Hoefliger Verpackungsmaschinen GmbH, Allmersbach im Tal (DE)

(72) Inventors: Steffen Gall, Allmersbach im Tal (DE); Daniel Mueller, Allmersbach im Tal (DE)

(73) Assignee: Harro Hoefliger Verpackungsmaschinen GmbH, Allmersbach im Tal (DE)

( * ) Notice: Subject to any disclaimer, the term of this patent is extended or adjusted under 35 U.S.C. 154(b) by 422 days.

(21) Appl. No.: 16/366,601

(22) Filed: Mar. 27, 2019

(65) Prior Publication Data

US 2019/0298614 A1 Oct. 3, 2019

(30) Foreign Application Priority Data

Mar. 28, 2018 (EP) ..................................... 18164596

(51) Int. Cl.
*A61J 3/07* (2006.01)
*A61K 9/48* (2006.01)

(52) U.S. Cl.
CPC ................ *A61J 3/074* (2013.01); *A61J 3/071* (2013.01); *A61K 9/4816* (2013.01)

(58) Field of Classification Search
CPC . A61K 9/4816; A61J 3/071; A61J 3/74; A61J 3/75; A61J 3/074; A61J 3/075
USPC .......................................... 53/281, 284, 287
See application file for complete search history.

(56) References Cited

U.S. PATENT DOCUMENTS

| | | | | |
|---|---|---|---|---|
| 1,073,286 A | * | 9/1913 | Remington | A61J 3/075 141/246 |
| 1,147,512 A | * | 7/1915 | Kirkland | A61J 3/075 141/241 |
| 1,567,639 A | * | 12/1925 | Eastman | A61J 3/075 53/390 |

(Continued)

FOREIGN PATENT DOCUMENTS

DE 102010038544 A1 4/2011
DE 202011003680 U1 6/2011

(Continued)

*Primary Examiner* — Robert F Long
*Assistant Examiner* — Eduardo R Ferrero
(74) *Attorney, Agent, or Firm* — Walter Ottesen, P.A.

(57) ABSTRACT

A capsule socket of a filling machine for two-piece capsules and a socket system having such a capsule socket and a capsule half of a two-piece capsule are disclosed herein. The two-piece capsules have two capsule halves, each with a capsule base and a capsule wall. The capsule socket includes a main body having a receiving space for the capsule half formed therein. The receiving space has a base portion, assigned to the respective capsule base, and a circumferential wall portion for centering the capsule wall. The receiving space has a clamping portion between the base portion and the circumferential wall portion. The clamping portion has a smaller free cross section than the circumferential wall portion. In the transition region from its base to its wall, the capsule half has a capsule part diameter. The clamping portion has a free clamping diameter, which is smaller than the capsule part diameter.

8 Claims, 2 Drawing Sheets

(56) References Cited

U.S. PATENT DOCUMENTS

| | | | | |
|---|---|---|---|---|
| 1,993,716 A * | 3/1935 | Hanley | A61J 3/074 | 53/281 |
| 2,742,749 A * | 4/1956 | McGuire | A61J 3/075 | 53/268 |
| 3,324,902 A * | 6/1967 | Lense | A61J 3/074 | 141/1 |
| 3,501,894 A * | 3/1970 | Takeuchi | B65B 1/10 | 53/281 |
| 3,552,095 A * | 1/1971 | Inman | A61J 3/075 | 53/390 |
| 3,675,390 A * | 7/1972 | Austin | B65B 43/40 | 53/282 |
| 3,933,239 A * | 1/1976 | Yoshida | A61J 3/074 | 198/384 |
| 4,040,536 A * | 8/1977 | Schwarz | A61J 3/071 | 220/8 |
| 4,196,564 A * | 4/1980 | Bodenmann | A61J 3/071 | 53/471 |
| 4,615,165 A * | 10/1986 | Gamberini | A61J 3/074 | 53/109 |
| 5,081,822 A * | 1/1992 | Boyd | A61J 3/074 | 53/281 |
| 5,321,932 A * | 6/1994 | Sundberg | A61J 3/075 | 53/281 |
| 5,417,030 A * | 5/1995 | Ribani | A61J 3/074 | 53/281 |
| 6,367,228 B1 | 4/2002 | Wurst et al. | | |
| 7,343,724 B1 * | 3/2008 | Williams | A61J 3/074 | 53/471 |
| 8,561,282 B2 * | 10/2013 | Hirota | A61J 3/074 | 29/464 |
| 9,170,213 B2 | 10/2015 | Runft et al. | | |
| 9,629,781 B2 * | 4/2017 | Fulper | A61J 3/074 | |
| 2005/0217207 A1 * | 10/2005 | Konishi | A61J 3/074 | 53/53 |
| 2006/0157054 A1 * | 7/2006 | Kuehn | A61K 9/4816 | 128/200.23 |
| 2008/0219803 A1 * | 9/2008 | Runft | A61J 3/074 | 414/21 |
| 2010/0132705 A1 * | 6/2010 | De Vos | A61M 15/0021 | 128/203.21 |
| 2011/0016826 A1 * | 1/2011 | Schmied | A61J 3/074 | 53/267 |
| 2011/0097397 A1 * | 4/2011 | Wang | A61J 3/071 | 424/454 |
| 2011/0277300 A1 * | 11/2011 | Hirota | A61J 3/074 | 29/428 |
| 2014/0182587 A1 * | 7/2014 | Dunne | A61M 15/0086 | 128/203.15 |
| 2017/0333358 A1 * | 11/2017 | Stegemann | A61K 9/4808 | |

FOREIGN PATENT DOCUMENTS

| | | |
|---|---|---|
| WO | 2008141861 A1 | 11/2008 |
| WO | 2011047945 A2 | 4/2011 |

* cited by examiner

CAPSULE SOCKET FOR TWO-PIECE CAPSULES AND SOCKET SYSTEM

CROSS REFERENCE TO RELATED APPLICATION

This application claims priority of European patent application no. 18 164 596.1, filed Mar. 28, 2018, the entire content of which is incorporated herein by reference.

FIELD OF THE INVENTION

The invention relates to a capsule socket of a filling machine for two-piece capsules and to a socket system including such a capsule socket.

BACKGROUND OF THE INVENTION

Particularly in the pharmaceutical sector, but also in the area of nutritional supplements or the like, use is made of capsules that can be swallowed and that are filled with active substance preparations or the like. Capsules of this kind are in two parts, being composed of two capsule halves, namely a capsule bottom and, mounted on the latter, a capsule top. Commonly used capsule materials include hard gelatin, HPMC (hydroxypropyl methylcellulose) or the like.

Empty capsules are supplied for filling in a loosely connected state and fed to a capsule transport system. The latter includes a segment system with capsule sockets, namely with capsule top sockets and with capsule bottom sockets, wherein the loosely connected empty capsules initially come to lie in the capsule top sockets. Proceeding from this state, the capsule bottom is pulled out of the capsule top, for example via underpressure, and introduced into a receiving space of the capsule bottom socket. The filling of the capsule bottom takes place in the capsule bottom socket. Thereafter, the capsule bottom is pressed toward the capsule top socket, for example via a ram, and is then inserted there into the capsule top.

A circumferential wall portion of the receiving space serves to loosely center the capsule wall. It should be noted here that the individual capsule parts have certain divergences or tolerances in their external dimensions. It may also happen that capsules have to be processed which, while having identical nominal dimensions, have different mechanical behaviors resulting from different materials. With the aim of ensuring that such capsule halves can be freely inserted into the respective capsule sockets and can also be ejected from these again, the prior art provides for suitably generous dimensioning of the receiving space with play, particularly in the region of its circumferential wall.

In such a scenario, a critical effect lies in what is called capsule rebound. The capsule bottoms are in the first instance correctly introduced or sucked into the receiving space of the respective capsule sockets, which process takes place at high speed. On termination of the impulse-like underpressure surge, the capsule bottoms may bounce off the base and in so doing perform the capsule rebound. The rebound of a capsule bottom may also have repercussions on the capsule top lying above it, the capsule top for its part then having a tendency toward capsule rebound. In a less critical case, time is lost until all of the capsule halves have settled in their position and the filling operation can be started. In a more critical case, individual capsule halves are no longer back in their intended position or even spring out of their socket. This results in the production of waste material or even in a production shutdown. The stated effect can be alleviated by a more closely toleranced adaptation of the socket geometry to the respective capsule types that are to be processed. However, this assumes that an adapted set of capsule sockets is present for each specific type of capsule. A universal use for different capsules within a defined diameter range is thus lost and, in addition, complete avoidance of capsule rebound is not possible.

SUMMARY OF THE INVENTION

It is an object of the invention to develop a capsule socket in such a way that its operational reliability is enhanced.

This object can, for example, be achieved by a capsule socket of a filling machine for two-piece capsules, the two-piece capsules having two capsule halves, each capsule half having a capsule base and a capsule wall. The capsule socket includes: a main body having a receiving space for a capsule half formed therein; the receiving space having a base portion, assigned to the capsule base of the capsule half, and a circumferential wall portion for centering the capsule wall of the capsule half; the receiving space having a clamping portion between the base portion and the circumferential wall portion; the clamping portion having a first free cross section; the circumferential wall portion having a second free cross section; and, the first free cross section of the clamping portion being smaller than the second free cross section of the circumferential wall portion.

It is a further object of the invention to provide a socket system in which a capsule socket and a capsule half are adapted to each other in such a way that the capsule half can be easily engaged in and disengaged from the capsule socket but can nevertheless be held reliably in the latter.

This object can, for example, be achieved by a socket system having: a capsule socket; a capsule half having a capsule base and a capsule wall; the capsule socket including a main body having a receiving space for a capsule half formed therein; the receiving space having a base portion, assigned to the capsule base of the capsule half, and a circumferential wall portion for centering the capsule wall of the capsule half; the receiving space having a clamping portion between the base portion and the circumferential wall portion; the clamping portion having a first free cross section; the circumferential wall portion having a second free cross section; the first free cross section of the clamping portion being smaller than the second free cross section of the circumferential wall portion; the capsule half having a capsule part diameter ($D_U$) in a transition region from the capsule base to the capsule wall; the clamping portion having a free clamping diameter ($D_K$); and, the free clamping diameter ($D_K$) being smaller than the capsule part diameter ($D_U$).

According to an aspect of the invention, a capsule socket is provided in which the receiving space has a clamping portion between the base portion and the circumferential wall portion, wherein the clamping portion has a smaller free cross section than the circumferential wall portion. In a corresponding socket system having such a capsule socket and a matching capsule half, the clamping portion of the receiving space has a free clamping diameter which is smaller than the capsule part diameter of the associated capsule half. In other words, it is not therefore the case that the entire receiving space is reduced in cross section so that the capsule half is guided and held with a clamping action. Rather, according to an aspect of the invention, only local clamping via the clamping portion is entailed. In this way, the capsule or the capsule half can be freely introduced or suctioned, while the clamping action of the clamping portion occurs only in the region of the end position, in which the capsule half is positioned as intended. Conversely, after the filling operation, all it takes is a brief thrust to free the capsule bottom from its clamped engagement, after which a free, unimpeded movement can take place for inserting it into the capsule top. The same also applies analogously for the subsequent ejection of the filled and connected capsule. The clamping action, limited in place to the clamping portion, ensures that the respective capsule half does not spring back again from its target position even during very rapid cycles or at a high speed of movement. Instead, the effect achieved is that the capsule halves have already adopted their filling position after just a very short time and are also retained for the subsequent filling process. Capsule rebounds are reliably avoided, such that operational reliability is considerably enhanced. Free mobility and a locally limited clamping action function within a considerable bandwidth of dimensional tolerances and mechanically different behaviors of various capsules, such that specific adaptation of the capsule sockets to defined capsule types is rarely if at all required.

In an embodiment, the clamping portion also has a smaller free cross section than the base portion. A particular mechanical property of the capsule bottom is exploited here: the dome-shaped capsule base is stiffer in the radial direction than the approximately cylindrical capsule wall. During the insertion process, therefore, the capsule base is initially constrained by the narrowed clamping portion, but it can then slightly widen again in the larger cross section of the base portion. With its smaller free cross section, the clamping portion only still engages around the softer, more yielding capsule wall. In this way, a locking action in accordance with the principle of a press stud is achieved through pure clamping. A precise and defined position of the capsule half is achieved, which acts only over a short axial path and in practice does not therefore adversely affect the free mobility of the capsule half during insertion or ejection. In particular, the clamping portion directly adjoins the base portion. In this way, the axial position of the capsule half is unambiguous and practically free of play in both directions, that is, from above and below.

It may be expedient to provide individual radial projections or the like on the inner wall of the receiving opening, in order thereby to form the clamping portion. In a preferred embodiment, the clamping portion is formed by an annular bead on the inside face of the receiving opening and in particular has a rounded cross section. The goal of achieving the desired clamping or locking action entails only very small local surface pressures acting on the capsule wall. The rounded cross section allows the capsule half to be engaged and disengaged without damage.

In an embodiment, the capsule socket is a capsule bottom socket for receiving a capsule half configured as a capsule bottom. In this way, it is possible to reliably avoid a situation where the capsule bottom, entering at high speed, bounces back from the base portion. Alternatively or in addition, it may be expedient that the capsule socket is a capsule top socket for receiving a capsule half configured as a capsule top. Reactions from the capsule bottom, or other influences, can no longer cause the capsule top to rebound.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
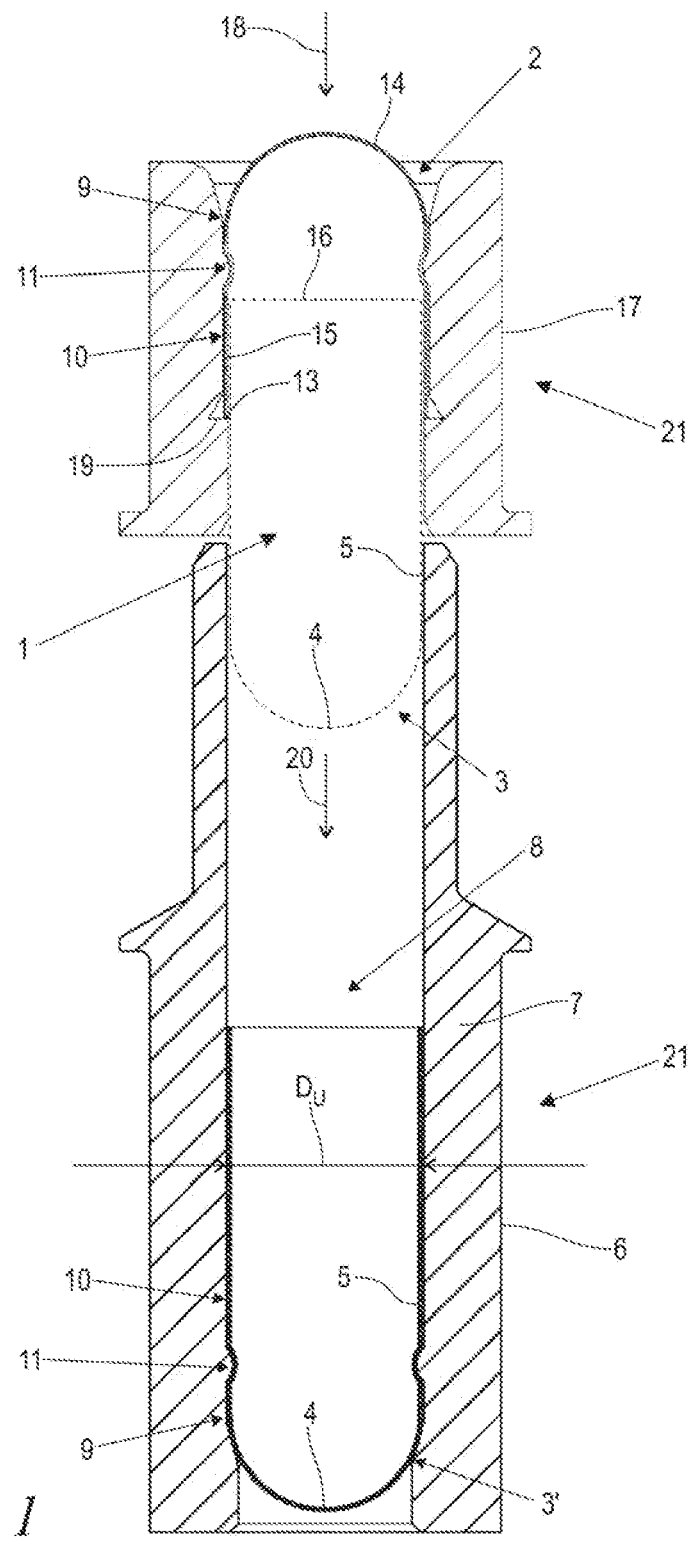
FIG. 1 shows a longitudinal sectional view of a socket system with a two-piece capsule, with a capsule bottom socket and with a capsule top socket for handling a capsule top and capsule bottom during filling.

FIG. 1 shows a longitudinal sectional view of a socket system, as part of a transport system (not shown) within a filling machine for two-piece capsules 1. The two-piece capsules 1, of which only a single specimen is shown here for the sake of greater clarity, are used for example in the pharmaceutical sector or in the area of nutritional supplements and, in the filled state, they contain an active substance preparation. In the state when finally filled and closed, they are intended to be swallowed by a person. Materials such as hard gelatin, HPMC or the like are examples of a capsule material that dissolves, after being swallowed, and releases the content of the capsule.

The two-piece capsule 1 is composed of two capsule halves, namely a capsule top 2 and a capsule bottom 3, wherein the capsule bottom 3 is pushed into the open side of the capsule top 2. In its usual configuration, the capsule top 2 has a hemispherical capsule base 14, which is adjoined by an upper capsule wall 15. At its open side, the capsule top 2 is delimited by a circumferential edge 13 of the upper capsule wall 15. The capsule bottom 3 is constructed analogously to the capsule top 2 and includes a hemispherical, dome-shaped capsule base 4, which is adjoined by a cylindrical lower capsule wall 5. At its side directed toward the capsule top 2 and inserted into the latter, the capsule bottom 3 is delimited by a circumferential edge 16 of the cylindrical capsule wall 5, and, when capsule top 2 and capsule bottom 3 are plugged together, a part of the cylindrical capsule wall 5 and of its circumferential edge 16 comes to lie inside the upper capsule wall 15 of the capsule top 2.

The socket system includes at least one of the aforementioned capsule halves, and at least one capsule socket 21 which is assigned to the capsule half and which is geometrically adapted to the capsule half in the manner described in detail below. This can be a capsule bottom socket 6 and a capsule half configured as a capsule bottom 3, or a capsule top socket 17 and a capsule half configured as a capsule top 2. In an illustrative embodiment shown, the capsule system includes a capsule bottom 3, a capsule top 2 and two associated capsule sockets 21, namely a capsule socket 21 configured as a capsule bottom socket 6 for receiving the capsule bottom 3, and a capsule socket 21 configured as a capsule top socket 17 for receiving the capsule top 2. In practical operation, several such socket systems are used simultaneously or synchronously.

Empty two-piece capsules 1 are supplied in a state in which the capsule bottoms 3 are loosely fitted in respectively assigned capsule tops 2. In this state, an individual capsule 1 is inserted into the capsule top socket 17 from above in accordance with arrow 18. The upper capsule socket 21 configured as the capsule top socket 17 includes a main body 7 and, formed in the latter, a receiving space 8 for the capsule top 2, wherein this upper receiving space 8 has a base portion 9, assigned to the capsule base 14 of the capsule top 2, and a circumferential wall portion 10 for centering the capsule wall 15. The receiving space 8 is part of a stepped through-bore, within which an annular support shoulder 19 adjoins the receiving space 8. The circumferential edge 13 of the capsule top 2 bears on a support shoulder 19 in the inserted state.

Underneath the capsule top socket 17, the capsule bottom socket 6 is positioned coaxially thereto and likewise includes a main body 7 and, formed in the latter, a receiving space 8 for a capsule half, here for the capsule bottom 3. The lower receiving space 8 also includes a circumferential wall portion 10 and, in this case below the latter, a base portion 9, wherein this base portion 9 is assigned to the capsule base 4 of the capsule bottom 3, and wherein the circumferential wall portion 10 serves to center the capsule wall 5 of the capsule bottom 3.

By means of vacuum or the like, for example, the capsule bottom 3 is pulled out of the capsule top 2 and sucked into the receiving space 8 of the capsule bottom socket 6 in accordance with arrow 20 until it comes to lie in its end position, labeled 3', with its downwardly facing capsule base 4 on the base portion 9, of reduced diameter compared to the circumferential wall portion 10, and is axially supported there from below in the rest state. Here, the capsule wall 5 of the capsule bottom 3 is centered by the circumferential wall portion 10 of the receiving space 8 and supported in the radial direction.

The capsule top socket 17 is now removed (in a manner not shown) such that the unit composed of capsule bottom 3 and capsule bottom socket 6 is freely accessible from above. The capsule bottom 3 is then filled with the active substance preparation (not shown) while it is held in the capsule bottom socket 6. After it has been filled, the two-piece capsule 1 is closed. For this purpose, the unit composed of capsule top 2 and capsule top socket 17 is moved back into the position according to FIG. 1, and the capsule bottom 3 is pressed back up into the capsule top 2, for example via a ram (not shown), counter to the arrow 20.

Figure 2:
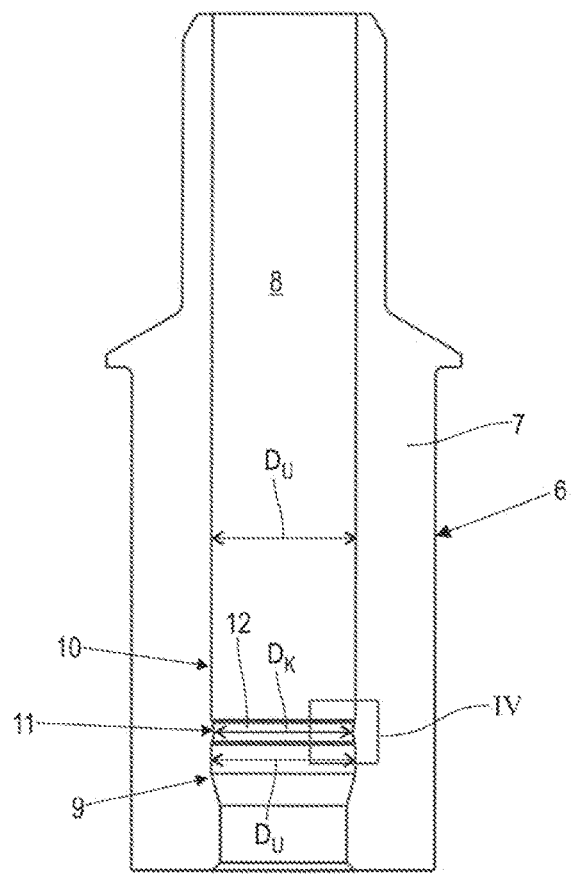
FIG. 2 shows a longitudinal sectional view of the capsule bottom socket according to FIG. 1, with details of its geometric configuration.

FIG. 2 shows a longitudinal sectional view of the capsule bottom socket 6 according to FIG. 1. From comparison with FIG. 1, it will be clear that the receiving space 8 formed in the main body 7, coaxially thereto, includes not only the aforementioned base portion 9 and the likewise aforementioned circumferential wall portion 10, but also a clamping portion 11 with reduced cross section. The clamping portion 11 is situated directly above the base portion 9, that is, directly adjoins the latter from above. The circumferential wall portion 10 is situated above it. However, it may also be expedient for part of the circumferential wall portion 10 to be located between the base portion 9 and the clamping portion 11. In any case, the geometry of the receiving space 8 is adapted to the geometry of the capsule bottom 3 in use, in such a way that the base portion 9 alone receives the hemispherical capsule base 4, while the clamping portion 11 located above it interacts with the capsule wall 5 of the capsule bottom 6 directly above the capsule base 4.

Comparison of FIGS. 1 and 2 also reveals that the clamping portion 11 has a smaller free cross section than the circumferential wall portion 10 and optionally also has a smaller free cross section than the base portion 9. In the present case, this is achieved by a defined clamping diameter $D_K$ of the clamping portion 11 as follows: The capsule bottom 3 according to FIG. 1 has a capsule part diameter $D_U$ along its capsule wall 5, at least in the transition of the capsule wall 5 to the capsule base. For free axial mobility of the capsule bottom 3 inside the receiving space 8, the free cross section of the circumferential wall portion 10 is adapted thereto and likewise has the capsule part diameter $D_U$, wherein slight radial play with respect to the capsule wall 5 may be expedient. The same also applies to the uppermost region of the base portion 9. At any rate, the clamping portion 11 has a smaller free cross section than the circumferential wall portion 10 and than the uppermost region of the base portion 9 adjoining the clamping portion 11, for which purpose the free clamping diameter $D_K$ is smaller than the capsule part diameter $D_U$ in the illustrative embodiment shown.

Figure 3:
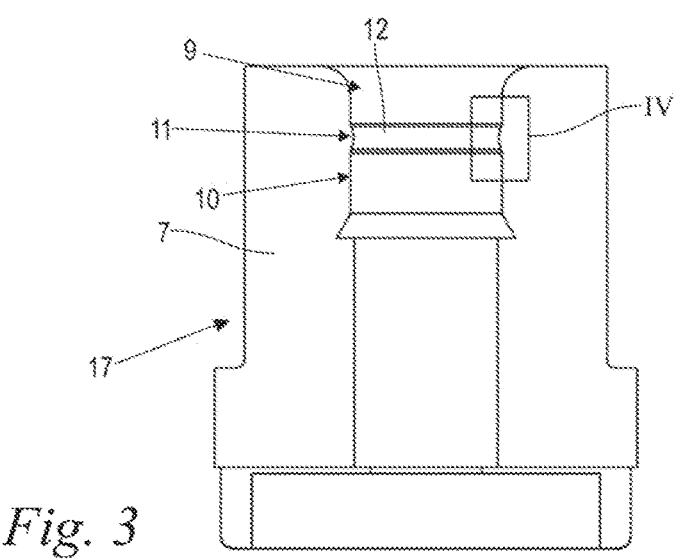
FIG. 3 shows a longitudinal sectional view of the capsule top socket according to FIG. 1, with details of its geometric configuration; and, FIG. 4 shows an enlarged view of the detail labeled IV in FIGS. 2 and 3 and concerning the cross-sectional shape of an annular bead for forming the clamping portion.

FIG. 3 shows a longitudinal sectional view of the capsule top socket 17 according to FIG. 1. It will be seen from comparison with FIG. 2 that the capsule top socket 17 according to FIG. 3 is constructed analogously to the capsule bottom socket 6 of FIG. 2 insofar as its receiving space 8 also has a clamping portion 11 between the base portion 9 and the circumferential wall portion 10. As regards the geometric configuration of the clamping portion 11, in particular its clamping diameter (not shown here) and its adaptation to the capsule part diameter (likewise not shown) of the capsule top 2 (FIG. 1), the observations made regarding the capsule bottom socket 6 according to FIG. 2 apply analogously.

Figure 4:
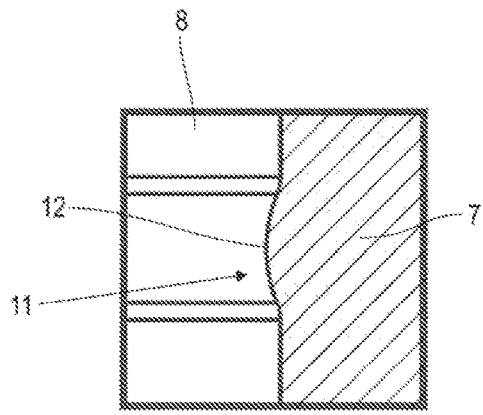

A detail labeled IV is indicated in each of FIGS. 2 and 3 and is shown enlarged in FIG. 4. According to the latter, the clamping portion 11 is formed by an annular bead 12 running round the inside face of the receiving space 8. In the preferred illustrative embodiment shown, the annular bead 12 has a rounded cross section. However, a cross section with corners, locking edges or the like may also be expedient. Moreover, within the scope of the invention, other configurations of the clamping portion are possible, for example, by arrangement of projections that protrude radially inwardly over the contour of the circumferential wall portion 10.

In any case, an embodiment according to the disclosure has the effect that the capsule bottom 3, directly after being pulled out of the capsule top 2 (FIG. 1), is clamped or locked via the clamping portion 11 when it reaches the base portion 9 and, as a result, cannot spring back from the base portion 9 (capsule rebound). For this purpose, the clamping portion 11 presses into the capsule wall 5 of the capsule bottom 3 directly above the capsule base thereof, wherein the capsule wall yields slightly in a radially inward direction under elastic deformation. Unimpeded filling of the capsule bottom 3 can take place. Conversely, a slight impulse from below suffices to then free the filled capsule bottom 3 from its clamped or locked engagement and to convey it back again to the associated capsule top 2. The same also applies analogously to the capsule top 2, which is held locked in the capsule top socket 17 and prevented from springing out. However, the completed two-piece capsule 1 can still be pushed out with just a slight thrust or impulse.

It is understood that the foregoing description is that of the preferred embodiments of the invention and that various changes and modifications may be made thereto without departing from the spirit and scope of the invention as defined in the appended claims.

What is claimed is:

1. A capsule socket of a filling machine for two-piece capsules, the two-piece capsules having two capsule halves, each capsule half having a capsule base, an open capsule end disposed opposite the capsule base, a capsule wall, and a transition region between the capsule base and the capsule wall, the capsule socket comprising:

a main body having a receiving space for a capsule half formed therein;

said receiving space having a base portion, assigned to the capsule base of the capsule half, and a circumferential wall portion for centering the capsule wall of the capsule half;

said receiving space having a clamping portion between said base portion and said circumferential wall portion;

said clamping portion having a first free cross section;

said circumferential wall portion having a second free cross section;

said first free cross section of said clamping portion being smaller than said second free cross section of said circumferential wall portion;

wherein said clamping portion directly adjoins said base portion; and, wherein said clamping portion is closer to the transition region of the capsule half than to the open capsule end when the capsule half is inserted in said capsule socket.

2. The capsule socket of claim 1, wherein said clamping portion has a smaller free cross section than said base portion.

3. The capsule socket of claim 1 further comprising:
an annular bead;
said annular bead being disposed on said inside face of said receiving space; and,
said clamping portion being formed by said annular bead.

4. The capsule socket of claim 3, wherein said annular bead has a rounded cross section.

5. The capsule socket of claim 3, wherein said annular bead is formed as a single component with the capsule socket.

6. The capsule socket of claim 1, wherein the two capsule halves include a capsule top and a capsule bottom, and the capsule socket is a capsule bottom socket for receiving the capsule bottom.

7. The capsule socket of claim 1, wherein the two capsule halves include a capsule top and a capsule bottom, and the capsule socket is a capsule top socket for receiving the capsule top.

8. A socket system comprising:
a capsule socket;
a capsule half having a capsule base, an open capsule end disposed opposite said capsule base, and a capsule wall;
said capsule socket including a main body having a receiving space for a capsule half formed therein;
said receiving space having a base portion, assigned to said capsule base of said capsule half, and a circumferential wall portion for centering said capsule wall of said capsule half;
said receiving space having a clamping portion between said base portion and said circumferential wall portion;
said clamping portion having a first free cross section;
wherein said clamping portion directly adjoins said base portion;
said circumferential wall portion having a second free cross section;
said first free cross section of said clamping portion being smaller than said second free cross section of said circumferential wall portion;
said capsule half having a capsule part diameter ($D_U$) in a transition region from said capsule base to said capsule wall;
said clamping portion having a free clamping diameter ($D_K$); and,
said free clamping diameter ($D_K$) being smaller than said capsule part diameter ($D_U$); and,
wherein said clamping portion is closer to said transition region of said capsule half than said open capsule end when said capsule half is inserted in said capsule socket.

* * * * *